(12) United States Patent
Sakowski et al.

(10) Patent No.: US 8,377,394 B2
(45) Date of Patent: Feb. 19, 2013

(54) SPIN COLUMN SYSTEM AND METHODS

(75) Inventors: Robert Sakowski, Barneveld, WI (US);
Scott Fulton, Middleton, WI (US)

(73) Assignee: Agilent Technoogies, Inc., Santa Clara, GA (US)

( * ) Notice: Subject to any disclaimer, the term of this patent is extended or adjusted under 35 U.S.C. 154(b) by 0 days.

(21) Appl. No.: 12/835,886

(22) Filed: Jul. 14, 2010

(65) Prior Publication Data

US 2011/0014722 A1   Jan. 20, 2011

Related U.S. Application Data

(60) Provisional application No. 61/313,390, filed on Mar. 12, 2010, provisional application No. 61/285,135, filed on Dec. 9, 2009, provisional application No. 61/225,674, filed on Jul. 15, 2009.

(51) Int. Cl.
*B01D 45/00* (2006.01)

(52) U.S. Cl. .......................... 422/533; 422/527; 422/553

(58) Field of Classification Search .................... 422/50, 422/407, 415, 417, 68.1, 69, 70, 72, 527, 422/533, 547, 548, 549, 550, 551, 552, 553; 435/288.6; 210/655, 656
See application file for complete search history.

(56) References Cited

U.S. PATENT DOCUMENTS

| 4,886,184 | A * | 12/1989 | Chamourian | 220/781 |
| 5,073,346 | A | 12/1991 | Partanen et al. | |
| 2002/0110495 | A1* | 8/2002 | Hunt et al. | 422/101 |
| 2002/0179520 | A1* | 12/2002 | Madden et al. | 210/416.1 |
| 2003/0147779 | A1* | 8/2003 | Azarani et al. | 422/99 |
| 2006/0124551 | A1 | 6/2006 | Gjerde et al. | |
| 2008/0176254 | A1 | 7/2008 | Fang et al. | |
| 2008/0206746 | A1* | 8/2008 | Jia | 435/6 |
| 2009/0223893 | A1 | 9/2009 | Gjerde et al. | |

FOREIGN PATENT DOCUMENTS

| WO | WO 01/66218 A1 | 9/2001 |
| WO | WO 02/053256 A1 | 7/2002 |

OTHER PUBLICATIONS

Qiagen website. Downloaded from <http://web.archive.org/web/20051015184955/http://www1.qiagen.com/resources/info/qiagen_purification_technologies_4.aspx> as accessed by the examiner on Oct. 28, 2011. Archived by the Internet Archive on Oct. 15, 2005.*
Chaiken, I.M., (1986) Quantitative High-Performance Affinity Chromatography: Evaluation of Use for Analyzing Peptide and Protein Interactions, *J. Chromatogr.*, 376:87-93.
Winzor, D., (2004) Determination of binding constants by affinity chromatography. *J. Chromatogr.*, 1037(1-2):351-367.

* cited by examiner

*Primary Examiner* — Yelena G Gakh
*Assistant Examiner* — Christopher A Hixson (57) ABSTRACT

The present invention provides a low bed-volume spin column system and methods of use. The system includes various combinations of spin columns with packed beds, a rack for holding the spin columns, a receiver plate that attaches to the rack and that has wells in registration with the spin columns held in the rack, a lid that attaches to the receiver plate and seals the spin columns, and an incubator block configured for accepting the wells of the receiver plate and for incubating the packed bed. The lid, spin columns, rack, receiver plate, and incubator block are preferably capable of being assembled in a nested configuration. In preferred versions of the invention, the rack is compatible with and attachable to conventional 96-well microplates. Further provided are methods of using the spin column system that include quantitatively purifying and analyzing an analyte, removing and preventing air entrainment within the packed bed, and incubating the packed bed while preventing drying thereof.

31 Claims, 5 Drawing Sheets

SPIN COLUMN SYSTEM AND METHODS

CROSS REFERENCE TO RELATED APPLICATIONS

This application claims priority under 35 USC §119(e) to U.S. Provisional Patent Application 61/313,390, filed Mar. 12, 2010; U.S. Provisional Patent Application 61/285,135, filed Dec. 9, 2009; and U.S. Provisional Patent Application 61/225,674, filed Jul. 15, 2009, each of which is incorporated herein by reference in its entirety.

FIELD OF THE INVENTION

The present invention is directed to a low bed-volume spin column system designed for assays that may involve quantitative binding and elution from solid phase supports and/or controlled-temperature chemical reaction.

BACKGROUND

Many applications in the fields of pharmaceuticals, food and beverage manufacturing, clinical diagnostics, and life science research require that the concentration of a particular target analyte be determined accurately and precisely. Target analytes are often contained in very complex mixtures with many other species of similar molecules. Common samples containing target analytes include blood, cell lysates, cell culture media, process flowstreams, etc.

A highly selective assay is required for accurate and precise quantitation of analytes in such complex samples. Common assays used for this type of analysis are immunoassays. In immunoassays, antibodies are used to bind a target and immobilize it on a solid phase surface. This binding enables the target to be separated from the other molecules in the liquid sample by washing away the non-bound molecules. Following this separation, a second antibody to the target labeled with a marker such as an enzyme, fluorescent dye, etc. is used to produce a signal to sensitively indicate the amount of target bound to the solid phase. In some versions the target analyte itself may be labeled to produce a detectable signal. Immunoassays are selective, i.e., capable of discriminating between the target and other molecule species in the sample. They are also highly sensitive, i.e., capable of measuring concentrations in the ng/mL range or below.

Immunoassays, however, suffer from serious drawbacks for some applications. Immunoassays are relatively complex, with complicated and expensive reagent requirements. They can be challenging to automate. In a number of fields such as the manufacture of biopharmaceuticals, there is a great need for high precision in manufacturing applications to track yield or mass balance in the manufacturing process. The target analyte may be the protein product itself in a process flowstream. The product concentrations in such manufacturing applications can typically be in the µg/mL to mg/mL range. Thus, the high sensitivity of the immunoassay (typically in the ng/mL range or lower) can be an issue. A dilution of several orders of magnitude is often needed to bring the sample concentration into the range of the assay. This adds substantially to the complexity of the assay, and makes it difficult to achieve the required precision or reproducibility.

One common approach for this type of application is to use a high performance chromatography (HPLC) column packed with a resin that binds the target analyte in a highly selective fashion. Typical resins include an immobilized affinity ligand that selectively binds the target analyte. Alternatively, a more conventional chromatographic resin (such as ion exchange or reversed phase) may be used to selectively separate the target. After injecting a sample into an HPLC column, the column is washed, and the analyte is eluted with an agent that releases the analyte from the immobilized ligand. The analyte may be quantified using ultraviolet (UV) absorbance in the HPLC detector. An example of this process is the use of a protein A HPLC column to measure therapeutic monoclonal antibody (IgG) concentrations in samples from a cell culture production system. Such a test is highly selective for the target (IgG in this case), operates in the µg-mg/mL range with no sample dilution, and has very high precision (usually <5% coefficient of variation (CV)). However, affinity HPLC requires a complex and expensive instrumentation system. The system can run only one sample at a time, and each sample run typically takes 5-15 minutes. Thus, throughput on this system is limited to 4-12 samples per hour.

One way to improve sample throughput is to run multiple columns and samples at a time. Large-scale multiplexing with conventional HPLC systems is difficult and expensive because separate pumps, injectors, columns, and detectors are required for each sample channel or column. However, a number of relatively high-throughput devices and methods have been developed for sample preparation through solid phase extraction that could be applied to this type of quantitative assay.

One such device is the pipet tip column, which uses an air displacement pipet to move liquid in and out through a disposable tip packed with a selective binding resin. Multichannel pipet systems (up to 96 or even 384 channels) can be used for high throughput applications. However, pipet tip columns have several disadvantages. The high-throughput platform requires an expensive automated robotic system. In addition, the flow of liquid through the packed bed in a pipet tip column is limited to a single port of entry and exit at the distal end of the tip. It is therefore very difficult to get quantitative washing and elution from the packed bed due to the mixing that occurs in both the pipet tip itself and the well containing the sample or wash buffer. Finally, the air-displacement method of moving the liquid makes it very difficult to control the flow rate of the sample, particularly at the relatively low flow rates required to obtain quantitative binding. Thus, while useful for qualitative sample preparation, pipet tip devices have proven to be unusable for quantitative analysis of targeted analytes.

An alternative type of high-throughput purification device uses a vacuum manifold to move liquid in a downward direction through multiple packed beds. Such devices are commonly used for solid phase extraction. As with the pipet tip columns, control of the flow rate is difficult, especially at the low flow rates required for quantitative extraction. Also, such manifolds must have columns present in all available vacuum positions or resulting vacuum leaks will render the device ineffective. This makes it difficult to modify the number of samples being run in a batch.

The use of gravity to draw the liquid downward through the packed bed is another purification method. For many applications, this is impractically slow. To speed the process, the columns may be placed in a centrifuge to increase the effective g-field to a level that provides a desired flow rate. Such "spin columns" are widely used for extracting a target from a sample in a variety of applications because they do not require complex instrumentation or equipment beyond widely available laboratory centrifuges. Virtually all commercially available spin columns are designed to work with common microcentrifuge tubes, which have an inner diameter (ID) of 9 mm and a volume of 1.5 or 2.0 mL. The outermost diameter of these devices must be significantly larger than 9 mm in order to prevent the resin-containing device from being driven into the tube. The resin bed volumes of these devices are typically 100 µL or greater.

For high-throughput analysis and convenient handling of large numbers of relatively small samples, it is highly desirable to be able to work within the Society for Biomolecular Sciences/American National Standards Institute (SBS/ANSI) microplate format standard. Many different types of standard microplates are available at low cost as molded plastic parts. Liquid handling devices, such as pipets, are also designed to work within the standard. The conventional SBS/ANSI 96-well microplates have wells spaced 9 mm on center. They are commonly designed for quickly reading the optical absorbance of all the wells using widely available optical plate readers.

Conventional spin column devices have several drawbacks. Currently available devices designed to work individually with microcentrifuge tubes are physically too large to function with microplates, both in terms of fitting into the 9 mm spacing and having a bed volume appropriate for the volume of the microplate wells. A number of multi-column spin column devices have been built that are in the form of microplates with a column in each well. If the user has 96 samples to run, these spin column plates work well. However, if fewer than 96 samples are to be run, the spin column plate is discarded after a first run, and the unused wells are wasted. Alternatively, the unused wells on the spin column plate are used in a second run, but this runs the risk of cross contamination. It would be advantageous to consume only one spin column per sample but to be able to collect the eluates in the wells of a conventional microplate for analysis.

Another drawback of conventional spin column devices is that they are susceptible to air entrainment. Air entrained within the spin column can have several deleterious consequences. These deleterious consequences include reduced flow rate which gives rise to flow rate variability between cartridges at a given "×g" force, as well as loss of binding capacity due to air blocking part of the packed bed. Both of these issues lead to greatly increased variability in the analytical results, and, in extreme cases, to air-locking of the cartridge which prevents the sample from being loaded at all. Trapped air bubbles, if large enough, can also reduce or block flow through the bed during centrifugation, particularly at the low g-fields required for quantitative binding. There is a need for spin column devices that are not susceptible to air entrainment.

Yet another drawback of conventional spin column devices is that they are susceptible to drying. Some types of solid phase supports spin column devices must be stored and shipped in a wet condition. These supports include common gel-type chromatography media such as agarose, dextran, cellulose, and various synthetic polymer hydrogel materials, such as poly(methacrylates). These materials can suffer irreversible collapse of the gel structure on drying, which significantly degrades performance. There is a need for spin column devices that are less susceptible to drying.

SUMMARY OF THE INVENTION

The invention provides a spin column system that addresses the drawbacks of conventional systems described above. In an exemplary version, the spin column system includes at least one spin column, a rack, and a receiver plate. The rack has at least one aperture passing therethrough, which is dimensioned and configured to releasably engage the spin column. The receiver plate has at least one corresponding well for each aperture in the rack. The rack and receiver plate are dimensioned and configured to engage one another such that the aperture and the well are in registration when the rack and the receiver plate are engaged. The packed bed of the spin column is disposed entirely between a bottom surface of the well and a well opening of the well when the rack and receiver plate are engaged and the spin column is disposed in the aperture.

In some versions, the rack, the spin column, and the receiver plate are preferably dimensioned and configured to suspend an outlet tip of the spin column within 5 mm of a bottom surface of the well of the receiver plate. A top surface of a top panel on the receiver plate preferably contacts a bottom surface of a top panel of the rack when the rack and the receiver plate are engaged. Furthermore, a side panel and a lip of the rack preferably contact a side panel and a lip of the plate, respectively, when the rack and the receiver plate are engaged. The side panel of the rack also preferably contacts the lip of the receiver plate when the rack and the receiver plate are engaged.

In some versions, rack is dimensioned and configured to engage with a microplate, such as a conventional 96-well microplate or another microplate suitable for analyzing a sample. In such versions, the rack, the spin column, and the microplate are preferably dimensioned and configured to suspend an outlet tip of the spin column within 5 mm of a well opening of the well. These versions may be combined with spin columns that include a packed bed with a volume capacity, wherein the volume capacity of the packed bed is at least about 5-fold lower or, in some cases, at least about 10-fold lower than a volume capacity of the well of the microplate. In one specific example, the volume capacity of the packed bed is about 60 µL or less. The volume ratios described herein provide the system with a volume capacity suitable for conducting analyses in a high-throughput manner, wherein the analyses involve quantitative elution from the spin column and addition of an analysis reagent equal in volume to the volume of the analyte solution.

In a specific version of the invention, the rack includes 96 apertures and the receiver plate includes 96 wells, and the apertures and the wells are arranged in an 8×12 array on 9 mm centers. This enables the system to be compatible with conventional SBS/ANSI 96-well microplates.

Some versions of the invention further include a lid dimensioned and configured to engage with the rack and contact the spin column. When the lid is engaged with the rack and is contacting the spin column, specifically an upper rim of the spin column, and when the rack is mounted on the receiver plate described herein, the assembly preferably forms a substantially sealed chamber. The chamber includes a sample cup of the spin column, the packed bed, and the well of the receiver plate. In some cases, the chamber is substantially sealed from excess evaporation therefrom by virtue of continuous contacts between the spin column and the rack, the rack and the plate, and the lid and the upper rim of the spin column.

Some versions of the invention further include an incubator block dimensioned and configured to contact a substantial fraction of an outer surface of the well of the plate. The incubator block is further configured and to heat and cool to a specified temperature for a specified amount of time. The lid, spin column, receiver plate, and incubator block are preferably configured and dimensioned to assemble in a nested configuration.

The invention also provides methods of using the spin column system described herein. One method is a method of analyzing an analyte. The method includes, as a first step, inserting the spin column in the aperture in the rack and engaging the rack with the receiver plate, wherein the spin column, the rack, and the receiver plate form an assembled unit, and wherein the spin column is in register with the well in the receiver plate. The method further includes the steps of loading a sample in the spin column, spinning the assembled unit wherein an analyte in the sample binds to a packed bed in the spin column, washing non-binding sample components from the packed bed, eluting the analyte or a derivative thereof from the packed bed, and analyzing the analyte or the derivative thereof.

The spinning step preferably includes spinning the assembled unit in a centrifuge such that liquid added to the spin column is pushed under a centrifugal force through the packed bed of the spin column and into the well of the plate. As used herein, "binds to a packed bed" includes binding of the analyte to an immobilized affinity reagent or other selective binding surface in a packed bed of adsorbent particles for separation or purification thereof. During the spinning step, the analyte is quantitatively bound and retained in the packed bed. In some versions, the washing or eluting steps include adding to the spin column a volume of a wash or elution buffer at least five times a volume capacity of the packed bed, spinning the assembled unit, and collecting the flow-through in the well, wherein the well has a volume capacity at least 5-fold greater than the volume capacity of the packed bed. In other versions, the well has a volume capacity at least 10-fold greater than the volume capacity of the packed bed, and the analyzing includes adding to the well a volume of analytical reagent at least equal to the volume of the elution buffer, mixing the eluate and analytical reagent to create a mixture, and reading the mixture. The analyzing step preferably includes quantitating an amount of analyte. Other types of analyses described in the examples, described elsewhere herein, or known in the art are also acceptable. The system used in this method is configured such that after the analyzing step, the spin column can be removed from the rack and the method can be repeated with a second spin column, or set of spin columns, using the same rack.

Some versions of the method further include, prior to the loading step, rewetting the packed bed, wherein the rewetting comprises adding an amount of liquid to the spin column and spinning the assembled unit using the receiver plate at a high speed, wherein after the spinning step, the amount of liquid fills the receiver plate well to a level at least equal to an interface between the packed bed and a sample cup in the spin column, wherein a portion of liquid remains in the sample cup after spinning, and wherein air is removed from the packed bed.

Some versions of the invention include performing the inserting, loading, and spinning steps with a receiver plate as described herein. The receiver plate can then be removed and replaced with a conventional 96-well microplate or other plate suitable for analyzing a sample, wherein the analyte is collected in a well of the microplate during the elution step. Subsequent analyzing steps are also performed with the microplate.

Some versions of the invention include performing the inserting, loading, and spinning steps with a receiver plate as described herein to bind the analyte to the packed bed. This is followed by a step of loading a liquid containing a catalytic reagent such as an enzyme into the spin column, spinning the liquid into the packed bed to expose the enzyme to the bound analyte in the packed bed, incubating the assembly on an incubator block to allow the enzyme-catalyzed reaction to occur at a controlled temperature, and eluting the resulting reaction products, such as a derivative of the analyte, from the spin column into a plate such as a receiver plate.

In some versions, the method further includes engaging a lid with the rack to form a substantially sealed chamber comprising a sample cup of the spin column, the packed bed, and the well of the receiver plate. Forming such a chamber protects the spin columns during shipment of the assembly. Forming such a chamber also minimizes evaporation from the system, particularly during incubation of wells of the receiver plate in an incubator block. In other versions, the method includes incubating the wells of the receiver plate in an incubator block after the eluting step to promote evaporation of the elution buffer from the analyte.

The present invention provides a modular system for purifying, chemically reacting, and analyzing analytes in a sample in a high-throughput manner. It allows consumption of only one spin column per sample, even when fewer than 96 samples are used, but enables collection and analysis of the analyte in conventional 96-well microplates using common methods. The packed bed-to-well volume ratios disclosed herein permit analysis of the analyte by a number of common methodologies in a quantitative and high-throughput manner. The system described herein is also configured to prevent drying and air entrainment of packed beds.

The objects and advantages of the invention will appear more fully from the following detailed description of the preferred embodiment of the invention made in conjunction with the accompanying drawings.

DETAILED DESCRIPTION OF THE INVENTION

The spin column system generally includes a combination or any subcombination of a spin column 10, a microplate 20, a receiver plate 30, a rack 50, a lid 70, and an incubator block 80.

Figure 1:
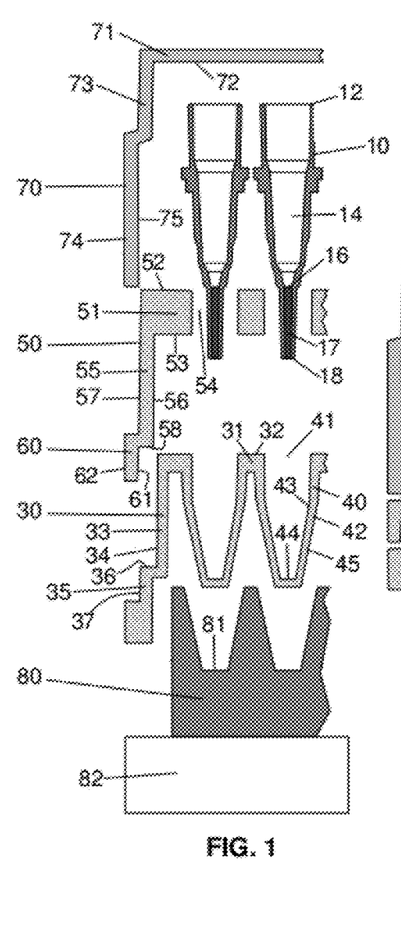
FIG. 1 depicts an exploded, side elevation cutaway view of a lid, spin columns, rack, receiver plate, and incubator block of the present invention.

Spin Column 10 and Packed Bed 17:

An exemplary version of the spin column 10 is shown in FIGS. 1-3 and 5-8. Referring specifically to FIG. 1, the spin column 10 includes a sample cup 14 in fluid communication with a packed bed 17. The sample cup 14 has an inlet defined by an upper rim 12 of the spin column 10 at one end and an interface 16 with the packed bed 17 at an opposing end. The sample cup 14 defines a cavity and has a volume capacity sufficient for holding a volume of sample, wash solution, elution buffer, or other liquid. The sample cup 14 and/or the sample cup inlet is preferably dimensioned and configured to receive a pipet tip therein for ease of liquid delivery.

The packed bed 17 is comprised of a liquid-permeable solid phase, such as particles (gel particles or otherwise) or a membrane, etc. Suitable solid-phase materials include common gel-type chromatography media such as agarose, dextran, cellulose, and various synthetic polymer materials, such as poly(methacrylates) and poly(styrene-divinylbenzene), and various inorganic materials such as silica, alumina, carbon and glass. The packed bed 17 is in fluid communication with the sample cup 14 via the interface 16 at one end and opens to an outlet tip 18 of the spin column 10 at an opposing end. The outlet tip 18 defines an opening to allow fluids to flow therethrough to exit the spin column 10 upon leaving the packed bed 17. The liquid volume capacity of the packed bed 17 is preferably between about 0.5 and 500 µL, more preferably about 1 and 250 µL, and most preferably between about 5 and 100 µL, such as about 5, 10, 20, 30, 40, 50, 60, 70, 80, or 90 µL or ranges therebetween.

The packed bed 17 is structured to selectively bind the target analyte. The packed bed 17 may be able to bind the target analyte on its own through a suitable selective binding surface or through a surface coating, or may have a reagent capable of carrying out the binding conjugated thereto such as an affinity reagent.

Suitable selective binding surfaces or coatings include hydrophobic or hydrophilic surfaces (for normal and reverse-phase, hydrophobic interaction and hydrophilic interaction) and positively or negatively charged surfaces (for ion exchange). Suitable affinity reagents include any substance that specifically and selectively binds an analyte through affinity recognition and attractive forces. Affinity recognition, often resembling the relationship between lock and key, is highly specific for the target and usually has a dissociation constant below $10^{-8}$ M (Winzor D. J., J. Chromatogr. 2004 1037(1-2): 351-67; Chaiken I. M., J Chromatogr. 1986, 376: 11-32). Suitable affinity reagents include antibodies, proteins, peptides, affibodies, minibodies, aptamers, nucleotides (RNA or DNA), polymers, metal chelate ligands, small molecules, and others.

The analyte captured by the packed bed 17 of selective adsorbent particles can be any molecule or substance in a sample for which analysis, purification, characterization, quantitation, or chemical modification is desired. Examples of analytes generally include but are not limited to proteins, peptides, nucleotides, carbohydrates, synthetic compounds and small molecules, and specifically include antigens, RNA, DNA, and complexes thereof, etc. In some instances, the analytes may include subcellular organelles, cells, and microorganisms. The specific analytes are usually mixed or complexed in samples with other non-analyte substances prior to purification and/or analysis with the system described herein. The analytes that bind specifically to the binding surface, surface coating, or affinity reagent can be separated from non-analyte substances in a given mixture of analytes and non-analyte substances with the system described herein. As used herein, "analyte" also includes reactants that bind to the packed bed 17, and "derivative of the analyte" includes reaction products derived from the reactants.

Examples of possible analyte-affinity reagent binding pairs include but are not limited to antibody-antigen and antibody-hapten pairs; receptor-ligand binding pairs; nucleic acid hybridizing oligomers (e.g., DNA or RNA fragments); artificial binding partners (e.g. molecular imprinting—the process of making molecule casts of small molecules by combining a resin with the small molecule, cross-linking or otherwise hardening the resin, grinding the resin and extracting the small molecule resulting in small molecule-specific casts capable of specifically binding the small molecule); and RNA nexamers—functionalized RNA oligomers capable of acting as a specific binding partner.

With a spin column 10 structured and configured as described herein, a liquid is introduced into the sample cup 14 via the sample cup inlet. The liquid may contain an analyte or buffer components required for washing away non-binding sample elements or eluting the bound analyte from the packed bed. Upon application of a centrifugal force, the liquid proceeds through the packed bed 17 and exits the packed bed through the outlet tip 18. Analytes become bound to the packed bed 17. Wash or elution liquids are introduced and spun through the packed bed in a similar fashion.

Figure 8:
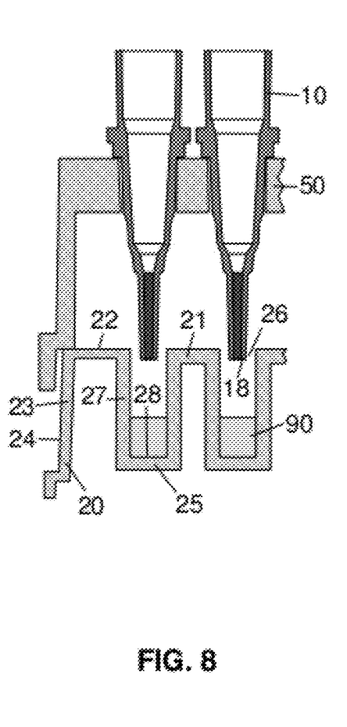
FIG. 8 depicts a side elevation cutaway view of spin columns and a rack of the present invention assembled with a conventional microplate for elution therein prior to quantitation and/or analysis.

Microplate 20:

An exemplary version of the microplate 20 is shown in FIG. 8. The exemplary microplate 20 includes a top panel 21 with an upper surface 22 and a side panel 23 with an outer surface 24. The microplate 20 further includes wells 25 defined within the top panel 21. The wells 25 include a well opening 26 in a plane defined by the top panel 21, well walls 27, and a bottom surface 28. The wells 25 of the microplate 20 preferably define a cylindrical shape with the well walls 27 defining planes substantially orthogonal to the plane defined by the microplate top panel 21, and the bottom surface 28 defining a plane substantially parallel to the plane defined by the microplate top panel 21. The bottom surface 28 may also have a rounded or conical bottom. The microplate 20 can have any number of wells 25 in any configuration. However, a preferred microplate 20 includes 96 wells distributed across the top panel 21 9-mm on center in an 8×12, two-dimensional rectangular array. Exemplary microplates for use with the present invention include conventional, SBS/ANSI-formatted, 96-well microplates. Other microplates are also suitable.

The microplate 20 is structured to receive liquid 90 eluted from the spin column 10 and, in some cases, additionally structured and/or configured to perform downstream analyses of analytes in the liquid 90 eluted from the spin column 10. For downstream analyses, the wells 25 in the microplate 20 may include reagents. In some cases, the reagents are chemically conjugated to inner surfaces of the wells 25, such as the bottom surface 28. Such reagents may include any reagent now known or discovered in the future involved in analyte detection or analysis, including antibodies, ligands, enzymes, cofactors, coenzymes, proteins, etc. Microplates configured for performing enzyme-linked immunosorbant assays (ELISAs), for example, are commercially available from Greiner Bio-One (Kremsmünster, Austria).

The spin column 10 and the well 25 are preferably positioned in registration, i.e., positioned relative to each other so that the outlet tip 18 of the spin column 10 is positioned directly over or centered with respect to the well 25. This enables collection of the eluate as it is eluted from the packed bed 17 through the outlet tip 18. Such positioning may be achieved, for example, by use of a rack 50 (discussed in detail below).

The spin column 10 and the well 25 are preferably coordinately dimensioned and configured to enable quantitative purification and analysis of an analyte. For quantitative purification and analysis to be accurate and reproducible, two distinct requirements should be met. First, the elution volume should be sufficient to completely elute all of the bound analyte. For chromatographic columns, at least five bed volumes of elution buffer should be used for complete, quantitative elution. Second, all of the eluate from the packed bed 17 plus the required volume of any colorimetric or fluorometric assay reagent (if used) should be able to fit within the volume of a single optical microplate well 25. This avoids the need to transfer the liquid into separate wells 25 for quantitative analysis, which would complicate the assay and make it less reproducible.

These two requirements combine to place an upper limit on the volume capacity of the packed bed 17 in the spin column 10 relative to the volume capacity of the well 25. If the eluate is analyzed directly, the volume capacity of the well 25 should be about or at least five-fold higher than that of the packed bed 17 to allow for quantitative elution from the packed bed 17. Methods of directly analyzing the eluate are described below. If an analytical reagent such as a colorimetric or fluorometric reagent is used in the analysis, the ratio of the volume capacity of the well 25 relative to that of the packed bed 17 is greater. Typically, the added volume of the assay reagent should be at least equal to the volume of the sample solution being analyzed. The volume capacity of the well 25 in a preferred version is therefore about or at least ten-fold higher than that of the packed bed 17 to accommodate the eluate (5× the packed bed 17) in addition to the assay reagent. Other volume capacities of the well 25 are acceptable, with the well 25 having a volume capacity about or at least about 0.5-fold, 2-fold, 5-fold, 20-fold, 50-fold, or 100-fold the volume capacity of the packed bed 17. Conversely, the packed bed 17 of the present invention preferably has a volume capacity at least about 5-fold lower than the volume capacity of the well 25, such as a volume capacity of about 10-fold, 50-fold, or 100-fold lower than the volume capacity of the well 25.

Conventional SBS/ANSI-formatted 96-well microplates suitable for optical detection in plate readers have wells with approximately a 300-µL volume capacity or less. An exemplary version of the current invention is formatted to be compatible with such conventional microplates. Accordingly, packed beds 17 of the current invention formatted for use with conventional microplates in direct analysis should have volume capacities of about 60 µL or less, such as 60, 50, 40, 30, 20, 10, 5, 2.5, or 1 µL or a volume capacity therebetween. Packed beds 17 for use with conventional microplates in analyses using colorimetric or fluorometric reagents should have volume capacities of about 30 µL or less, such as 30, 20, 10, 5, 2.5, or 1 µL or a volume capacity therebetween.

Receiver Plate 30:

An exemplary receiver plate 30 is shown in FIGS. 1-7. Referring to FIG. 1, the exemplary receiver plate 30 includes a top panel 31 with an upper surface 32, a side panel 33 with an outer surface 34, and a lip 35 offset from the side panel 33 that has an upper surface 36 and an outer surface 37. The receiver plate 30 further includes wells 40 defined within the top panel 31. The wells 40 include a well opening 41 in a plane defined by the top panel 31 and well walls 42 with an inner surface 43 and an outer surface 45. The inner surface 43 includes a bottom surface 44 as a sub-portion thereof. The wells 40 of the receiver plate 30 preferably define a frustoconical shape with the well walls 42 being angled in a manner that decreases the cross-sectional diameter of the well 40 from the well opening 41 to the bottom surface 44. The bottom surface 44 preferably defines a plane substantially parallel to a plane defined by the receiver plate top panel 31 but can also be rounded or concave. The receiver plate 30 can have any number of wells 40 in any configuration. However, a preferred receiver plate 30 includes 96 wells distributed across the upper panel 9-mm on center in an 8×12, two-dimensional rectangular array. Receiver plates 30 and microplates 20 designed for use together have the same number of wells 40,25 having the same distribution and configuration across the top panels 31,21. The receiver plate 30 is preferably made of thin-walled plastic but can be made from any other material.

As depicted in FIGS. 2, 3, 6, and 7, the receiver plate 30 is structured to store liquids 90 in the wells 40, immerse the outlet tip 18 of the spin column 10 in the liquids 90 stored in the wells 40, receive liquids 90 eluted from the spin column 10 and, in some cases, additionally structured and/or configured to perform downstream analyses of analytes in the liquid eluted from the spin column 10. The wells 40 in the receiver may include the same reagents as described above for the microplate 20 and may have the same volume capacities relative to the volume capacities of the packed bed 17 as described above for the microplate 20.

The spin column 10 and the well 40 are preferably positioned relative to each other so that the outlet tip 18 of the spin column 10 is centered with respect to the well 40 in registration. The outlet tip 18 is preferably positioned slightly above the bottom surface 44 of the well 40. This enables immersion of the outlet tip 18 in a very small volume of liquid 90 stored in the well 40 in addition to collection of the liquid 90 as it is eluted from the packed bed 17 through the outlet tip 18. Such positioning may be achieved by use of a rack 50 (discussed in detail below). In some versions, the spin column 10 and the well 40 may be coordinately structured and configured to enable quantitative purification and analysis of an analyte, as described herein for the microplate 20.

Rack 50:

An exemplary rack 50 is shown in FIGS. 1-3 and 5-8. Referring specifically to FIG. 1, the exemplary rack 50 includes a top panel 51 with an upper surface 52 and a lower surface 53; an aperture 54 defined within the top panel 51; a side panel 55 with an inner surface 56, an outer surface 57, and a bottom surface 58; and a lip 60 offset from the side panel 55 and having an inner surface 61 and an outer 62 surface.

Figure 2:
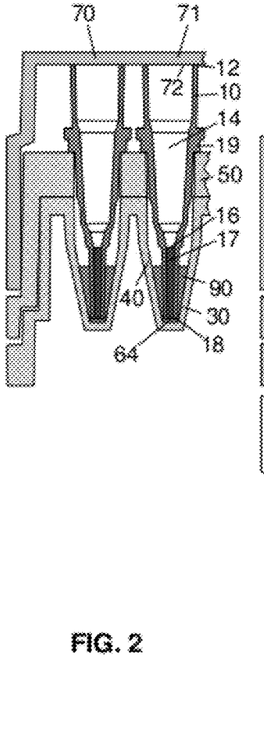
FIG. 2 depicts a side elevation cutaway view of a lid, spin column, rack, and receiver plate of the present invention assembled in a nested configuration.

The rack 50, and more specifically the aperture 54, is structured to securely but releasably hold the spin column 10 therein. A ridge 19 surrounding the outer perimeter of the spin column 10, as shown in FIG. 2, provides a stop to prevent the spin column 10 from falling through the aperture 54 and to enable the spin column 10 to be suspended within the rack 50. An optional taper of the spin column 10 together with a corresponding taper of the aperture 54 facilitate the secure support of the spin column 10 within the rack 50 and preferably facilitate a continuous contact between the spin column 10 and the rack 50. As used herein, "continuous contact" refers to contact between two objects without gaps therebetween.

The rack 50 is structured to suspend the outlet tips 18 of the spin columns 10 in registration over the center of the wells 40,25 of the receiver plate 30 and/or the microplate 20. This is achieved by the rack 50 having the same number of apertures 54 with the same distribution and configuration across the top panel 51 as the wells 40,25 in the receiver plate 30 and/or the microplate 20. The apertures 54 in the rack are also therefore in registration with the wells 40,25 in the receiver plate 30 and/or the microplate 20. The rack 50 may include any number of apertures 54, including one, two, or more, in any configuration. In a preferred version, the rack 50 contains 96 apertures 54 spaced 9-mm on center in an 8×12, two-dimensional rectangular array to enable use with conventional 96-well microplates 20 and/or similarly formatted receiver plates 30. Accordingly, spin columns 10 used with such a rack 50 are sized so that the spin columns 10 can be arranged within the rack 50 in the two-dimensional array with the outlet tips 18 spaced 9 mm on center. The spin columns 10 in this arrangement are positioned with their longitudinal axes oriented vertically. However, the rack 50 may also be configured to hold spin columns 10 in any desired configuration or geometry.

The rack 50 is configured and dimensioned to securely and releasably mount on the microplate 20 and/or the receiver plate 30 to suspend the spin column 10 in registration over the center of the wells 25. The rack 50 mounted on the microplate 20 is depicted in FIG. 8. To enable such mounting of the rack 50 on the microplate 20, the microplate 20 and the rack 50 are preferably coordinately structured wherein the bottom surface 58 of the side panel 55 of the rack 50 contacts and is supported on the upper surface 22 of the microplate 20 when the rack 50 is mounted on the microplate 20. (Refer to FIG. 1 for numbering of rack 50 elements.) This preferably creates a space between the top panel 51 of the rack 50 and the top panel 21 of the microplate 20. In addition, the inner surface 56 of the lip 60 of the rack 50 preferably contacts the outer surface 24 of the side panel 23 of the microplate 20. The contacts between the rack 50 and the microplate 20 are preferably continuous contacts.

As shown in FIG. 8, the microplate 20, rack 50, and spin column 10 are preferably structured such that when the spin column 10 is mounted in the rack 50 and the rack 50 is mounted on the microplate 20, the outlet tip 18 of the spin column 10 is suspended approximately in the plane, just above the plane, or just below the plane defined by the top panel 21 of the microplate 20. For example, the outlet tip 18 may be suspended at a distance of less than or equal to about 0, 0.01, 0.05, 0.1, 0.5, 1, 2.5, 5 mm from the plane defined by the top panel 21 of the microplate 20. This prevents liquid from missing the well 40 while being eluted from the outlet tip 18 and allows for the liquid to collect in the well 40 without submerging the outlet tip 18.

The rack 50 is also configured and dimensioned to securely and releasably mount on the receiver plate 30 to suspend the spin column 10 in registration over the center of the wells 40 of the receiver plate 30. To enable such mounting of the rack 50 on the receiver plate 30, the receiver plate 30 and the rack 50 are preferably coordinately structured wherein the receiver plate 30 and the rack 50 are capable of stacking in a nested configuration. Such a configuration is shown in FIG. 2. (Refer to FIG. 1 for numbering of rack 50 and receiver plate 30 elements.) Specifically, the top panel 51, side panel 55, and/or lip 60 of the rack 50 are preferably capable of being in contact with the top panel 31, side panel 33, and/or lip 35 of the receiver plate 30, respectively. More specifically, the lower surface 53 of top panel 51, the inner surface 56 of the side panel 55, the bottom surface 58 of the side panel 55, and/or the inner surface 61 of the lip 60 on the rack 50 are preferably capable of being in contact with the top surface 32 of the top panel 31, the outer surface 34 of the side panel 33, the upper surface 36 of the lip 35, and/or the outer surface 37 of the lip 35 on the receiver plate 30, respectively. The contacts between the rack 50 and the receiver plate 30 are preferably continuous contacts.

Figure 6:
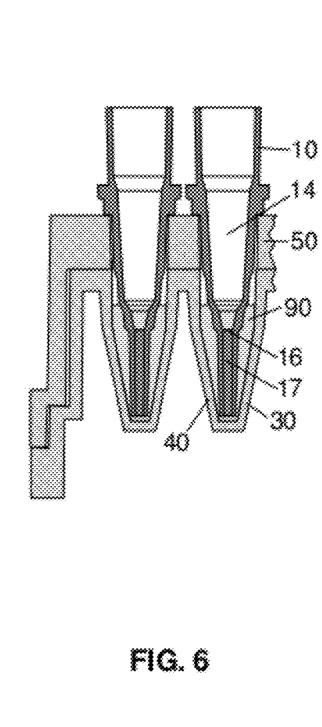
FIG. 6 depicts a side elevation cutaway view of spin columns, a rack, and a receiver plate of the present invention assembled in a nested configuration after rewetting.

In a preferred version of the invention, as shown specifically in FIG. 2, the spin columns 10 are suspended within the receiver plate 30 at a position to maintain immersion of the outlet tip 18 in a small volume of liquid 90 contained in the well 40 of the receiver plate 30. The receiver plate 30, rack 50, and spin column 10 are preferably structured such that when the spin column 10 is mounted in the rack 50 and the rack 50 is mounted on the receiver plate 30, the outlet tip 18 of the spin column 10 is suspended just above the bottom surface 44 of the receiver plate well 40 to define a minimal gap 64 therebetween. The gap 64 is preferably equal to or less than a distance between about 10 mm and 0.0001 mm, such as about 10 mm, 5 mm, 2.51 mm, 0.5 mm, 0.1 mm, 0.05 mm, 0.01 mm 0.005 mm, 0.001 mm, 0.0005 mm, or 0.0001 mm, or ranges therebetween. It is also preferred that the spin column 10 is suspended in the well 40 such that the interface 16 between the packed bed 17 and the sample cup 14 is below the plane defined by the well opening 41 so that liquid can fill the well 40 to a point above a plane defined by the interface 16 without the liquid spilling or overflowing from the well 40, as shown in FIG. 6.

The rack 50 is preferably capable of creating a continuous contact with both the spin column 10 and the receiver plate 30 when the spin column 10 is mounted in the rack 50 and the rack 50 is mounted on the receiver plate 30. Specifically, a continuous contact is preferably created between an outer surface of the spin column 10 and an inner surface of the aperture 54. A continuous contact is also preferably created between the lower surface 53 of the top panel 51 of the rack 50 and the top surface 32 of the top panel 31 of the receiver plate 30.

The receiver plates 40 and microplates 20 described herein are preferably capable of being used in combination with racks 50 and spin columns 10 in standard bench centrifuges with microplate rotors.

Figure 3:
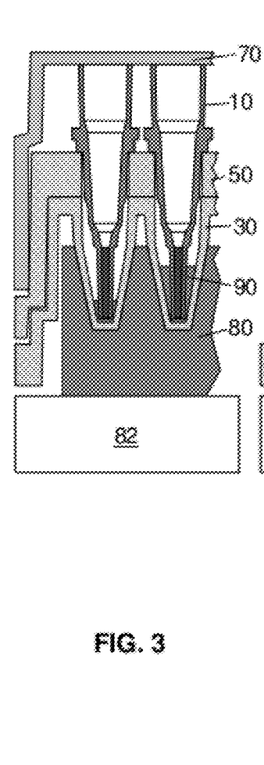
FIG. 3 depicts a side elevation cutaway view of a lid, spin column, rack, receiver plate, and incubator block of the present invention assembled in a nested configuration for incubation at controlled temperatures.

Lid 70:

An exemplary lid 70 is shown in FIGS. 1-3. Referring specifically to FIG. 1, the exemplary lid 70 includes a top panel 71 with a lower surface 72, a side panel 73, and an extended lip 74. The lip 74 is offset from the side panel 73 and includes an inner surface 75. The lid 70 fits over the top of the rack 50 with the spin column 10 mounted therein. Preferably, the fit of the lid 70 on the rack 50 is secure but loose enough so that the lid 70 can be removed, e.g., with a robotic gripper, without picking up the rack 50. The lid 70 is not secured vertically by any portion thereof on the rack 50, including any portion of the side panel 55. This ensures that when the lid 70 is mounted on the rack 50 with the spin column 10 mounted therein, the lower surface 72 of the lid 70 is capable of resting on the upper rim 12 of the spin column 10, preferably creating a continuous contact therebetween.

When the lid 70, rack 50, spin column 10, and receiver plate 30 are assembled as a single, nested unit (see FIGS. 2 and 3), continuous contacts between the lid 70 and the upper rim 12 of the spin column 10, between the rack 50 and the receiver plate 30, and between the spin column 10 and the rack 50 form a substantially sealed "chamber." The chamber includes the spin column sample cup 14, the packed bed 17, and the receiver plate well 40, which limits evaporation or spillage of liquids from the system. This is particularly useful for storage, shipment, or during incubations at elevated temperatures, as described below and shown in FIG. 3. The assembled system can be stacked on a standard robotic plate handler device and assembled or disassembled using standard robotic gripper systems found on automated liquid handlers.

Figure 4:
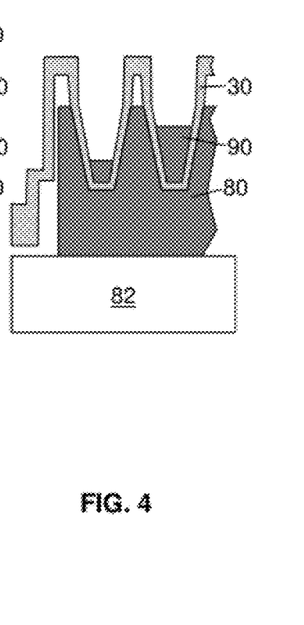
FIG. 4 depicts a side elevation cutaway view of a receiver plate and incubator block of the present invention in a nested configuration for evaporating liquid from wells of the receiver plate.

Incubator Block 80:

An exemplary incubator block 80 is shown in FIGS. 1, 3, and 4. Referring specifically to FIG. 1, the exemplary incubator block 80 includes incubator block wells 81. The incubator block 80 preferably has the same number of wells 81 with the same distribution and configuration as in the receiver plate 30. The incubator block wells 81 are shaped to directly contact a substantial portion, such as a majority, of the outer surface 45 of the receiver plate well walls 42. The incubator block 80 wells may contact greater than or equal to about 5%, 10% 20%, 30%, 40%, 50%, 60%, 70%, 80%, 90% or more or ranges therebetween of the outer surface 45 of the receiver plate 30 well walls 42. To achieve this contact, an incubator block 80 configured for use with a receiver plate 30 having frustoconical wells 40 will also have frustoconical wells 81. The incubator block 80 preferably comprises a metal such as aluminum or copper.

The incubator block 80 is preferably connected to a temperature-control device 82. The temperature device 82 may be configured to heat or cool the incubator block 80 at a specified temperature for a set amount of time and may be controlled by a temperature controller. The thermal mass and conductivity of the incubator block 80 is much greater than the thin-walled plastic receiver plate 30, and the conduction path through the receiver plate well walls 42 is relatively short. Therefore, any liquid in the well 40 quickly reaches the temperature of the incubator block 80 through thermal conduction.

As shown in FIG. 3, the lid 70, rack 50, spin column 10, receiver plate 30, and incubator block 80 are capable of being assembled in a nested configuration. This configuration is advantageous as the substantially sealed chamber resulting from the nesting of the lid 70, rack 50, spin column 10, and receiver plate 30 minimizes evaporation of liquid from the chamber when the receiver plate 30 is heated by the incubator block 80.

The system may comprise any number of spin columns 10 and corresponding receiver plate wells 40, rack apertures 54, incubator block wells 81, and microplate wells 25. This includes as few as one and as many as 96 or more. A preferred version of the system is dimensioned and configured to process up to 96 cartridges simultaneously, either manually or with a robotic system, and to function with conventional ANSI/SBS 96-well microplates.

Selectively Purifying and Quantitatively Analyzing an Analyte:

Using the elements described above, the current invention provides methods of selectively purifying and quantitatively analyzing an analyte from a sample. Such a method may include loading a sample containing an analyte in a sample cup 14, spinning the spin column 10 in a centrifuge to promote quantitative binding of the analyte to a affinity reagent in the packed bed 17, washing the remaining sample from the packed bed 17, eluting the analyte from the packed bed 17 into a well, and/or quantitating the amount of analyte in the eluate.

For quantitative binding, the spinning step must be performed under specific centrifugal forces. The centrifugal force must be high enough to generate a sufficient sample flow rate to move the sample through the packed bed 17. However, the centrifugal force must be low enough to permit the binding reaction between the analyte and the affinity reagent to reach equilibrium. If the binding does not reach equilibrium, the sample will not be bound and retained in the packed bed 17 in a quantitative manner. The centrifugal force enabling such quantitative binding is generally dependent on the volume capacity of the packed bed 17, with larger volume capacities using higher forces and smaller volume capacities using lower forces. Other dimensions such as length, radius etc. of the packed bed 17 may also affect the optimal force. In general, the centrifugal forces permitted for quantitative binding can be determined by splitting a single sample into equal parts and performing the current method using a variety of increasing centrifuge speeds in the spinning step. The permissive range is indicated by a peak in analyte recovery at a given centrifugal force or range of forces when analyte recovery is plotted as a function of centrifugal speed.

The washing step comprises loading a wash buffer in the sample cup 14 and spinning the spin column 10 in a centrifuge. Several washes may be performed. The washing step removes from the packed bed 17 residual substances from the initial sample that are not bound to the affinity reagent. Acceptable wash buffers for specific applications are well-known in the art.

The eluting step comprises adding a volume of an elution buffer preferably at least five times the volume capacity of the packed bed 17, spinning the spin column 10 in a centrifuge, and collecting the eluate in a well having a volume capacity at least five-fold greater than the volume capacity of the packed bed 17. If quantitative analysis is later required, it is critical that this step be formed such that dissociation of the analyte from the affinity reagent also occurs at equilibrium. The elution buffer used and the flow rate of the elution buffer through the packed bed 17 are both factors in inducing dissociation in a quantitative manner. The particular elution buffer used is dependent on the particular analyte-affinity reagent interaction. Elution buffers for specific analyte-affinity interactions are well-known in the art. The flow rate is determined by the centrifugal force. Permissive centrifugal forces can be determined in a manner analogous to that described above for quantitative binding.

The quantitating step can be performed by any number of known methods. The quantitating is preferably performed with the use of a plate reader. Plate readers are well-known the art. A common plate reader has the capacity to detect such variables as optical absorbance, fluorescence intensity, luminescence, time-resolved fluorescence, and fluorescence polarization, etc.

One approach to quantitating the analyte is to simply measure the optical absorbance of the known volume of collected analyte at an appropriate wavelength. For example, proteins absorb light at 280 nm and DNA absorbs light at 260 nm. This method is simple and accurate. However, the method has limited sensitivity and dynamic range. It may not be suitable for some applications, particularly if the spin column 10 has limited volume capacity. More sensitivity and dynamic range may be gained by mixing the eluted analyte with an analytical reagent such as a colorimetric or fluorometric reagent, which effectively "amplifies" the optical signal. An example of this is the Bradford Reagent, which is commonly used for the determination of protein concentration in samples. The Bradford Reagent produces a color change when the Coomassie Blue contained within the reagent binds to the proteins in solution. These reagents are used for general quantitation of analytes such as proteins. The use of a reagent-based assay combined with the micro-scale, highly selective analyte separation system provided by the spin column device described herein provides improved simplicity, throughput, sensitivity, range, and reproducibility in a high-throughput manner.

The desired method of quantitation determines the volume capacity of the packed bed 17 relative to that of the well in which the eluate is collected. For example, if the sample is analyzed directly through optical absorbance, the volume capacity of the packed bed 17 is about or at least 5-fold higher than the volume capacity of the well. If the sample is analyzed with the use of an analytical reagent, the volume capacity of the packed bed 17 is about or at least 10-fold higher than the volume capacity of the well.

Figure 9:
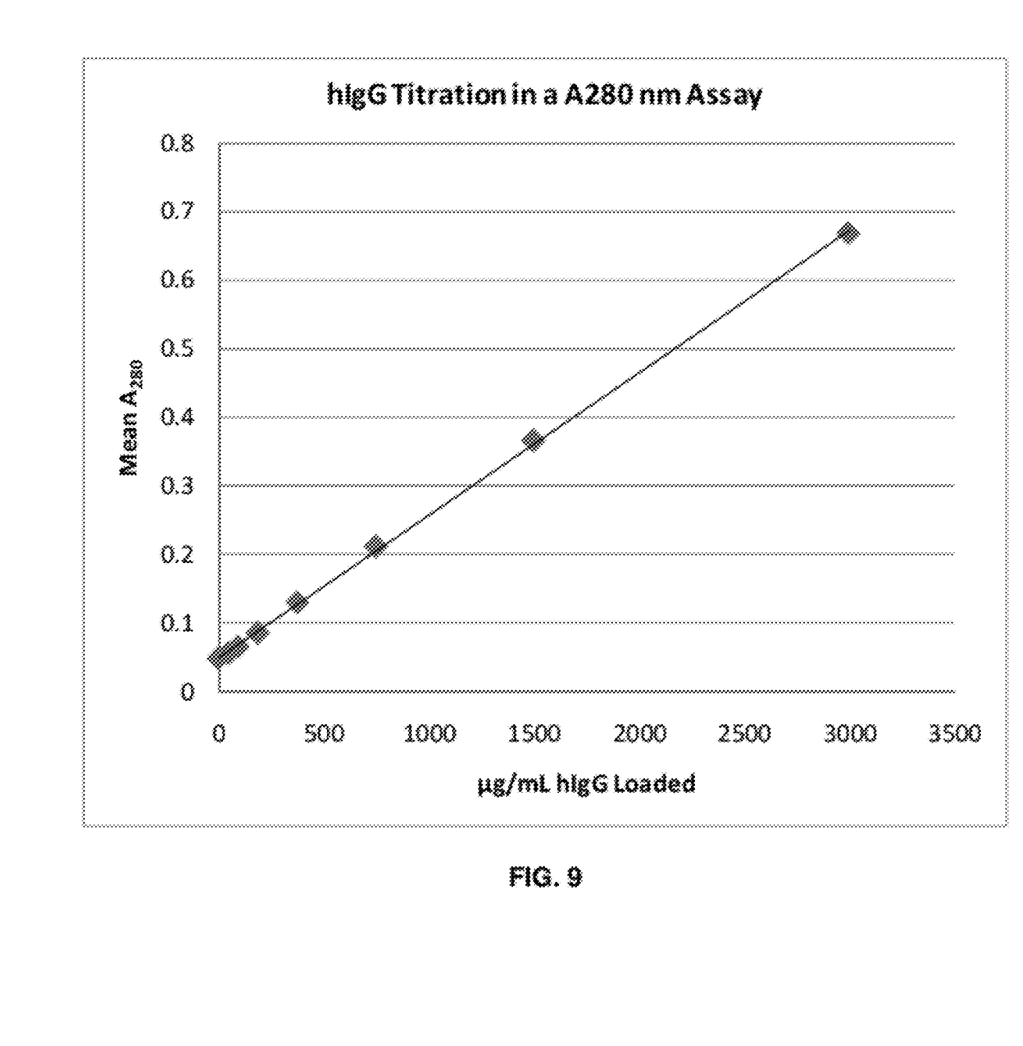
FIG. 9 is a graph showing the recovery of human IgG (hIgG) purified and quantitated with the spin column system of the present invention.

If quantitation of an analyte in a conventional microplate 20 is desired, the current method may be used with a rack as described herein. In such a case, a spin column 10 is inserted into an aperture 54 of the rack 50 and the rack 50 is mounted on a microplate 20 prior to eluting the analyte from the packed bed 17 (see FIG. 9). The spin column 10, rack 50, and microplate 20 are spun together and the analyte is collected in the well 25 of the microplate 20 for further analysis. Because the spin columns 10 can be removably inserted within the rack 50, fewer than all the apertures 54 in the rack 50 may be used per assay run. Thus, the rack 50 can accommodate a number of spin columns 10 corresponding to the exact number of samples to be analyzed. This prevents wasteful consumption of spin columns 10 if fewer than 96 samples are to be analyzed. Furthermore, the rack 50 can be re-used in further assay runs. A spin column 10, rack 50, and microplate 20 combination provides a modular platform for purifying and analyzing analytes from a sample. Similar modularity can be achieved with the receiver plate 30.

Further examples of components and methods associated with affinity purification and/or analysis that can be used in the present invention are found in U.S. Pub. No. 2008/0176254 (U.S. application Ser. No. 11/874,884), incorporated herein by reference in its entirety.

Chemically Reacting Immobilized Reactants:

The current invention also provides methods of chemically reacting immobilized reactants in a sample in a high-throughput manner. In these applications, a reactant is immobilized on the solid phase support material by hydrophobic and/or ionic adsorption, covalent binding, or selective binding, such as through an affinity ligand. A small volume of a reaction solution containing a catalytic reagent is exchanged into the solid phase of the packed bed 17. Exchange of the reaction solution in the packed bed 17 permits conversion of the reactants into products. The reaction products are preferably immediately released into the liquid phase. For purposes of analysis, it is critical to recover all of the liquid in fluid connection with the packed bed 17, especially because the desired reaction products can potentially diffuse out of the packed bed 17. Once the reaction is complete, the released reaction products and/or immobilized reactants may be recovered by elution from the spin column 10 in one or more subsequent steps. As described above, "analyte" includes the reactants, and "derivative of the analyte" includes the reaction products.

For promoting interaction between the reactant and the catalytic reagent, the reactant itself is immobilized on the packed bed 17, and the reaction reagent is maintained in solution. This configuration confers a number of benefits. First, the binding of the reactant can be highly selective, enabling it to be purified from a crude sample mixture prior to reaction. Second, the reaction time can be controlled to be as long as necessary for the reaction to reach completion (which is often much longer than the residence time that can be obtained by spinning liquid through the packed bed 17). Finally, the temperature of the reaction (which is also often critical) can be precisely controlled through the use of the receiver plate 30 and incubator block 80. Precise temperature control is very difficult to achieve during centrifugation.

Various catalytic chemical reactions that may be performed by catalytic reagents in the packed bed 17 include but are not limited to esterifications, isomerizations, oxidations, reductions, cyclizations, hydrolysis reactions, and labeling reactions. Suitable catalytic reagents include enzymes, coenzymes, cofactors, metals, ions, and any other catalysts. Enzymes useful in the invention include all classes of enzymes that have been employed for synthetic purposes, either by themselves, with appropriate cofactors, or with other enzymes in multienzyme processes. Examples of enzymes that have been utilized for synthetic purposes include but are not limited to PNGaseF, alkaline phosphatase, cellulase, catalase, lysozyme, urease, papain, trypsin, chymotrypsin, subtilisin, thermolysin, horse radish peroxidase, xanthine oxidase, glucose oxidase, horse liver alcohol dehydrogenase, invertase, ficin, bromelin, pepsin, heparinase, sulfatase, sucrose synthetase, aldolase, aspartase, fumarase, betagalactosidase, porcine pancreatic lipase, *Rhizopus* lipase, *Aspergillus niger* lipase, *Candida cylindraceae* lipase, *Mucor mihei* lipase, *Pseudomonas fluorescens* lipase, pig liver esterase, penicillin acylase, and horse liver esterase. Labeling compounds or hydrolyzing reagents may also be used as catalytic reagents.

Reactants can be any organic or inorganic solute that can be chemically transformed by a catalyst into a reaction product. Organic reactants include nucleotides, nucleic acids, amino acids, proteins, peptides, carbohydrates, sugars, glycoproteins and small molecules. Useful reactants which can be employed singly include various carbohydrate compounds that can be isomerized, such as glucose and sucrose, as well as squalene-like compounds that can be cyclized. Useful reactant pairs include esters-water, nitriles-water, amides-water, olefins-water, acids-alcohols, anhydrides-alcohols, anhydrides-amino acids, esters-amines, aldehydes-hydroxyketones, aldehydes-cyanohydrins, nitrile oxides-olefins, oxirane-water, and olefins-amines. Cofactor-mediated reductions involving enzyme catalysts include ketone, aldehyde, and olefin substrates. Similarly, oxidations have involved alcohol, aldehyde, ketone, sulfide, and various aliphatic and aromatic hydrocarbon substrates.

The washing and eluting steps may comprise adding a volume of a wash or elution buffer at least five times the volume capacity of the packed bed 17, spinning the spin column 10 in a centrifuge, and collecting the eluate in a well having a volume capacity at least five-fold greater than the volume capacity of the packed bed 17. The method of chemically reacting an immobilized reactant into one or more products as described above can be used with the described method of selectively purifying and/or quantitatively analyzing an analyte, wherein the product from the reaction constitutes a derivative of the analyte.

Temperature-Controlled Incubation and Reduction of Evaporation Resulting Therefrom:

It is very often advantageous and sometimes essential to carry out reactions as described above at controlled (typically elevated) temperature. In these cases, it is necessary to control the temperature of the packed beds 17 mounted in the rack 50, as well as any liquid 90 within and in contact with the packed beds 17. It has been found that simply placing the assembled system in an oven or temperature-controlled chamber is ineffective, since the conduction of heat by air into the plastic parts and thus into the liquid samples and packed beds 17 is very slow.

In the exemplary version of the invention shown in FIGS. 2 and 3, for example, the rack 50 and receiver plate 30 system is configured to hold the spin columns 10 in a position such that the outlet tip 18 of the spin column 10 is immersed in a volume of liquid 90 in the receiver plate well 40. It has been found experimentally that heat is transferred efficiently through the liquid 90 in the well 40 and into the packed bed 17, thereby rapidly and effectively controlling the temperature in the packed bed 17. Such efficient heat transfer occurs even if a very small amount of liquid 90 is present in the well 40. The temperature in the packed bed 17 equilibrates with the incubator block 80 almost as rapidly as the liquid 90 in the well.

The volumes in the packed bed 17 and associated liquid volumes for most applications are preferably quite small (typically 5-100 µL). This leads to the potential for evaporation during elevated temperature incubation. Configuring the system to hold the spin columns 10 in a position such that the outlet tip 18 of the spin column 10 is immersed in a volume of liquid 90 in the receiver plate well 40 (see FIGS. 2 and 3) helps prevent the packed bed 17 from drying out during elevated temperature incubation. Any liquid evaporating out of the top of the packed bed 17 will be replaced by liquid that wicks up from the receiver plate well 40. In addition, continuous contacts between the lid 70 and the upper rims 12 of the spin columns 10, the rack 50 and the receiver plate 30, and the spin columns 10 and the rack 50 that form the substantially sealed chamber (see FIGS. 2 and 3) limit the amount of evaporation from the system as a whole.

In use, a reaction solution is placed into the spin column sample cup 14 and centrifuged with a receiver plate 30 mounted under the rack 50 at a force low enough so that the reaction solution enters within the packed bed 17 but does not empty from the packed bed due to capillary action. The system at this step preferably includes a volume of liquid within the receiver plate wells 40 (see FIG. 2). The assembled system is then mounted onto the incubator block 80 with the lid 70 in place for incubation (see FIG. 3). A chemical reaction occurs during the incubation, which generates reaction products. The reaction products can be eluted without any volume loss by pipetting an elution solution into the spin column sample cup 14 and centrifuging into the same or different receiver plate 30. All of these operations can be carried out directly using standard robotic plate and liquid handling systems.

In some cases, it is desirable to evaporate some or all of the liquid from a sample after the reaction has occurred. For example, the eluted reaction products might need to be exchanged into a different solvent from the reaction solution for a subsequent cleanup step. The system of the present invention can be used for these drying steps by, for example, employing only the receiver plate 30 and incubator block 80, as shown in FIG. 4. This effectively "unseals" the substantially sealed chamber and permits evaporation. By using the same receiver plate 30, liquid transfer steps can be eliminated, thereby reducing sample loss and streamlining overall workflow.

Air Entrapment:

The present invention also provides a system and method that reduces air from being entrained within the packed bed 17 prior to and during use. Air can enter the packed beds 17 of spin columns 10 in several ways. First, in general handling and running of the columns 10, air can become entrained in the packed bed 17. Second, if the "×g" force used in spinning the columns 10 exceeds a certain critical value (which depends upon the diameter of the packing particles and the surface tension of the liquid phase on the beads), the centrifugal g field will force liquid out of the bed after reaches the top surface of the bed, pulling-in air behind it. Third, as soon as a sample cup 14 of the spin column 10 is empty during a run, liquid begins evaporating from both the top and bottom of the packed bed 17. Because of the very small bed volume (and thus liquid volume contained within the bed, which may be as little as 2 to 3 µL), significant air can enter the bed 17 due to this evaporation in just 10 to 15 minutes. Finally, in the very small devices of this invention, it is also possible to trap air bubbles in the confined area of the sample cup 14 just above the top of the packed bed 17 during introduction of samples and buffers by pipetting. The spin column system and associated methods described herein prevents these problems.

Figure 5:
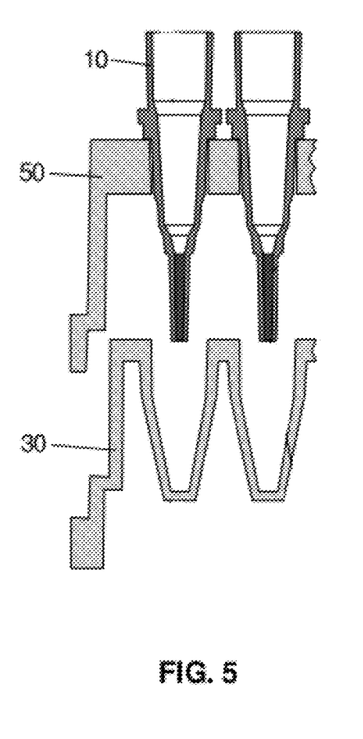
FIG. 5 depicts a side elevation cutaway view of spin columns, a rack, and a receiver plate of the present invention with the spin columns assembled in the rack.

The spin columns 10 in a system shown in FIG. 5, for example, can be prepared for use in a rewetting step to remove air that may be trapped in the packed bed 17. In the rewetting step, the rack 50, spin columns 10, and receiver plate 30 are assembled together as shown in FIG. 6. An amount of liquid 90 is added to the sample cup 14 of each spin column 10 and the assembly is spun in a centrifuge. Spinning the assembly equilibrates the liquid level in the spin column 10 with that in the receiver plate well 40 wherein the level of liquid inside the well 40 of the receiver plate 30 and inside the sample cup 14 of the spin column 10 are the same (see FIG. 6). The amount of liquid added to the sample cup 14 and spun is preferably sufficient so that the equilibrated level of liquid is above the interface 16 of the packed bed 17 and at least some liquid remains in the sample cup 14 (see FIG. 6).

The rewetting step can be performed at relatively high centrifugal force (e.g., about 1000×g or more). This generates sufficiently high flow rate such that all of the trapped air within the packed bed 17 is removed. Keeping the final liquid level above the top of the packed bed 17 (see FIG. 6) prevents the bed from being "spun dry" by the high centrifugal force, keeps it from drying out over time by being constantly immersed in liquid, and fills the most constricted area of the sample cup 14 of each spin column 10 with liquid to prevent air bubbles from being entrained in the packed bed 17 during subsequent loading of material into the spin columns 10.

Figure 7:
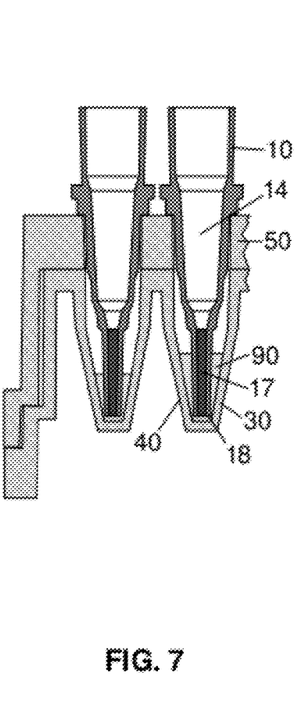
FIG. 7 depicts a side elevation cutaway view of spin columns, a rack, and a receiver plate of the present invention assembled in a nested configuration after loading.

After rewetting, a liquid sample can be loaded on top of the small amount of liquid contained in the sample cup of the spin column 10. The rack 50 and spin columns 10 are then removed from the receiver plate 30, and the receiver plate 30 is emptied or replaced. The rack 50 and spin columns 10 are then placed on an empty receiver plate 30 and spun with the receiver plate 30 in place. Wash steps are similarly performed. As shown in FIG. 7, the conical shape of the wells 40 insures that after even a very small volume of liquid has passed through the bed, the outlet tip 18 is immersed in liquid in the plate well 40. This prevents evaporation inside the bed from the outlet tip-side 18 of the packed bed 17. In addition, if any evaporation occurs from the interface 16 of the packed bed 17, liquid will wick up from the corresponding well 40 in the receiver plate 30 due to capillary action. This wicking action prevents the packed bed 17 from drying out due to evaporation from the interface 16-side of the packed bed 17. At any point during the sequence of steps described herein, the receiver plate 30 can be easily separated from the rack 50 and be emptied or replaced.

A wide range of different volumes of liquid 90 can be loaded into the sample cup 14 of each spin column 10 during the loading step. All will pass through the packed bed 17 provided that the level of liquid in the corresponding receiver plate well 40 does not fill to a level above the interface 16. See FIG. 7.

A final step in any assay using this system involves eluting a separated, purified, isolated, or reacted analyte or derivative thereof (or desired fraction) from the packed bed 17 and collecting the analyte or derivative thereof (or fraction) in a microplate well 25 for analysis. For this step, the rack 50 containing the spin columns 10 are removed from the receiver plate 30 and assembled on the microplate 20, as shown in FIG. 8. The positioning of the outlet tip 18 at or just below the plane defined by the top panel 21 of the microplate 20 enables clean and accurate collection of all the liquid elution buffer added to the sample cups 14 after it has passed through the packed beds 17. The packed bed 17 of each spin column 10 is vulnerable to drying or air bubble entrapment at this stage, but it is always the last step in the process. Following this step, the spin columns 10 can be immediately rewet as described above and stored in a fully wet, air-free state.

The invention includes any individual element described herein or combinations thereof. The elements described herein can be used in any combination whether explicitly described or not. Any version of any method, element, or device of the invention may be used with any other method, element, or device of the invention. All combinations of method or process steps described herein can be performed in any order, unless otherwise specified or clearly implied to the contrary by the context in which the referenced combination is made.

As used herein, the singular forms "a," "an," and "the" include plural referents unless the content clearly dictates otherwise. The term "or" is generally employed in its sense including "and/or" unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All publications, patents, and patent applications are herein expressly incorporated by reference to the same extent as if each were specifically and individually indicated by reference. In case of conflict between the present disclosure and the incorporated publications, patents, and patent applications, the present disclosure should control.

The elements described herein can comprise, consist of, or consist essentially of the essential elements and limitations described herein, as well as any additional or optional steps, ingredients, components, or limitations described herein or otherwise useful in the art.

It is understood that the invention is not confined to the particular construction and arrangement of parts herein illustrated and described, but embraces such modified forms thereof as come within the scope of the claims.

EXAMPLES

Example 1

Spin columns were constructed using molded polypropylene housings, with a 5-μL-volume packed bed contained between molded-in filter supports and a 200-μL-volume sample cup (AssayMAP cartridges, BioSystem Development, LLC, Madison, Wis.). The packed bed consisted of polystyrene/divinylbenzene-based porous beads coated with a hydrophilic polymer with immobilized protein A affinity ligand (POROS MAb Capture A, Applied Biosystems, Inc., Foster City, Calif.). The spin columns were mounted in a rack constructed according to the present invention, which was in turn mounted on a receiver plate with 250 μL conical bottom wells, constructed according to the present invention.

The spin columns were supplied dry and thus had to be fully rewet before use. To accomplish this, 200 μL of a buffer liquid (50 mM phosphate pH 7.2, 150 mM NaCl) was pipetted into the sample cups of the spin columns. The spin column/ rack/receiver plate assemblies were placed in a centrifuge equipped with a microplate rotor (Model 5810, Eppendorf, Inc., Hauppage, N.Y.) and centrifuged at 1000×g for 2 minutes.

Following the centrifugation, the liquid level in the receiver plate wells was exactly at the liquid level in the spin column sample cups. The sample cups contained ~15 μL of liquid and the receiver plate wells contained ~185 μL. Microscopic examination of the packed beds indicated that the particles were fully hydrated and no air bubbles were present in either the packed beds or the sample cups.

Example 2

The spin columns described in Example 1 were rewet using the procedure described in that example. The receiver plate wells were emptied, and 25 μL of sample solutions containing varying concentrations of purified human IgG were pipetted into the sample cups of the spin columns. The assemblies were centrifuged at 50×g for 5 minutes, thereby exposing the IgG in the sample to the immobilized protein A at a relatively low flow rate to promote selective and quantitative binding of the IgG to the protein A by an affinity interaction. Then 50 μL of the buffer liquid was pipetted into each spin column sample cup, and the assemblies were centrifuged at 200×g for 2 minutes to wash. The wash step was then repeated. The receiver plates were then removed and replaced with 96-well, half area UV microplates with a working well volume of 175 μL (Model 675801, Greiner GmbH, Frickenhausen, Germany). 50 μL of an elution liquid (100 mM glycine, pH 2.0) was then pipetted into each spin column sample cup, and the assemblies were centrifuged at 200×g for 2 minutes to elute the bound IgG into the microplates. The plates were then read in a plate reader at 280 nm (SpectraMAX 250, Molecular Devices, Inc., Sunnyvale, Calif.). The results are shown in the following table and the graph in FIG. 9. The standard curve is highly linear ($R^2$=1.00001) with good precision (CV<6%).

| μg/mL hIgG | A280 nm | | | | | Standard | |
|---|---|---|---|---|---|---|---|
| | Rep 1 | Rep 2 | Rep 3 | Rep 4 | Mean | Deviation | % CV |
| 3000 | 0.594 | 0.631 | 0.634 | 0.592 | 0.613 | 0.023 | 3.7% |
| 1500 | 0.325 | 0.328 | 0.333 | 0.344 | 0.333 | 0.008 | 2.5% |
| 750 | 0.178 | 0.176 | 0.195 | 0.197 | 0.187 | 0.011 | 5.9% |
| 375 | 0.112 | 0.116 | 0.118 | 0.127 | 0.118 | 0.006 | 5.4% |
| 187.5 | 0.079 | 0.081 | 0.083 | 0.080 | 0.081 | 0.002 | 2.1% |
| 93.75 | 0.063 | 0.064 | 0.064 | 0.066 | 0.064 | 0.001 | 2.0% |
| 46.875 | 0.055 | 0.055 | 0.054 | 0.055 | 0.055 | 0.001 | 0.9% |
| 0 | 0.047 | 0.047 | 0.049 | 0.046 | 0.047 | 0.001 | 2.7% |

Example 3

Figure 10:
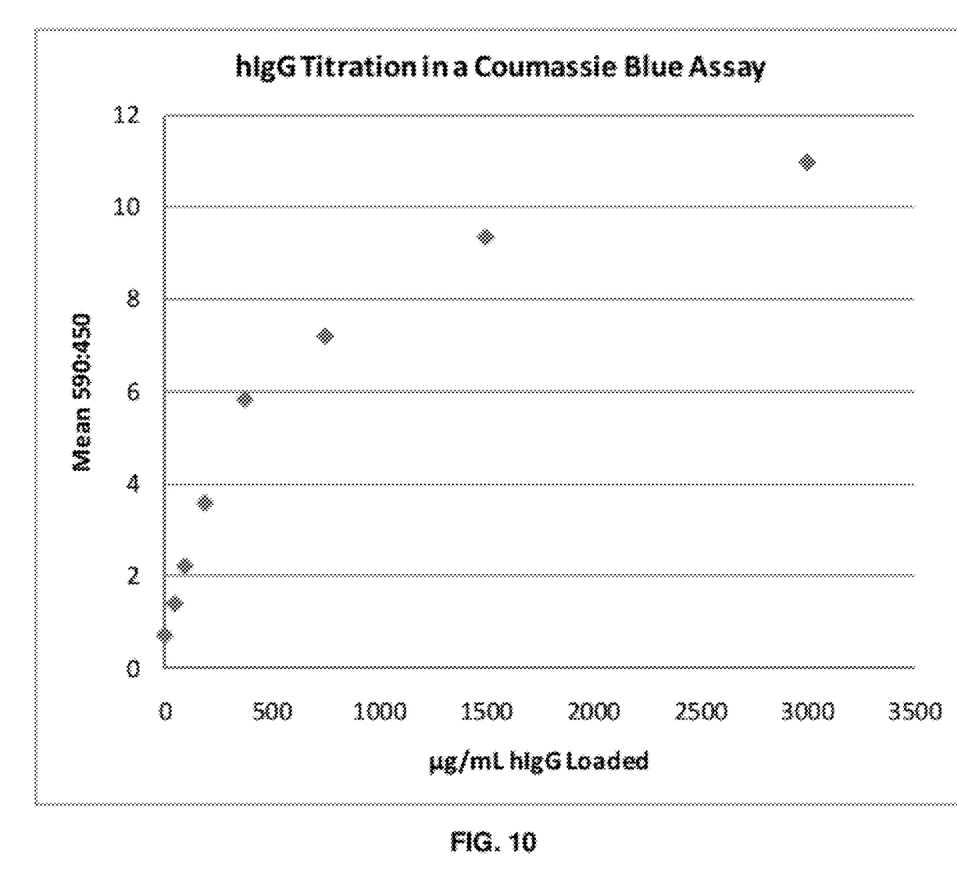
FIG. 10 is a graph showing the recovery of hIgG purified and quantitated using Coumassie Blue with the spin column system of the present invention.

In order to increase the sensitivity of the assay for the low IgG concentrations, 125 μL of Coumassie Blue protein assay reagent (Thermo Scientific, Inc., Waltham, Mass.) was added to each of the product wells from the experiment in Example 2, mixed and incubated for 10 minutes. The plates were read in the plate reader at 450 and 590 nm, and the ratio of the two absorbances was used for the readout. The results are shown in the following table and in the graph in FIG. 10. The results become non-linear above ~500 μg/mL, but the assay is ~10× more sensitive than the A280 nm assay shown in Example 2.

| µg/mL hIgG | A590 nm/A450 nm | | | | | | |
|---|---|---|---|---|---|---|---|
| | Rep 1 | Rep 2 | Rep 3 | Rep 4 | Mean | Standard Deviation | % CV |
| 3000 | 11.20 | 11.03 | 10.91 | 10.70 | 10.96 | 0.21 | 1.9% |
| 1500 | 9.39 | 10.07 | 9.21 | 8.69 | 9.34 | 0.57 | 6.1% |
| 750 | 7.37 | 7.45 | 6.57 | 7.38 | 7.19 | 0.42 | 5.8% |
| 375 | 5.78 | 5.98 | 5.40 | 6.13 | 5.82 | 0.31 | 5.4% |
| 187.5 | 3.33 | 3.86 | 3.08 | 4.01 | 3.57 | 0.44 | 12.3% |
| 93.75 | 2.13 | 2.31 | 1.92 | 2.44 | 2.20 | 0.23 | 10.2% |
| 46.875 | 1.37 | 1.45 | 1.27 | 1.44 | 1.38 | 0.08 | 5.9% |
| 0 | 0.70 | 0.71 | 0.71 | 0.70 | 0.71 | 0.00 | 0.7% |

Example 4

Figure 11:
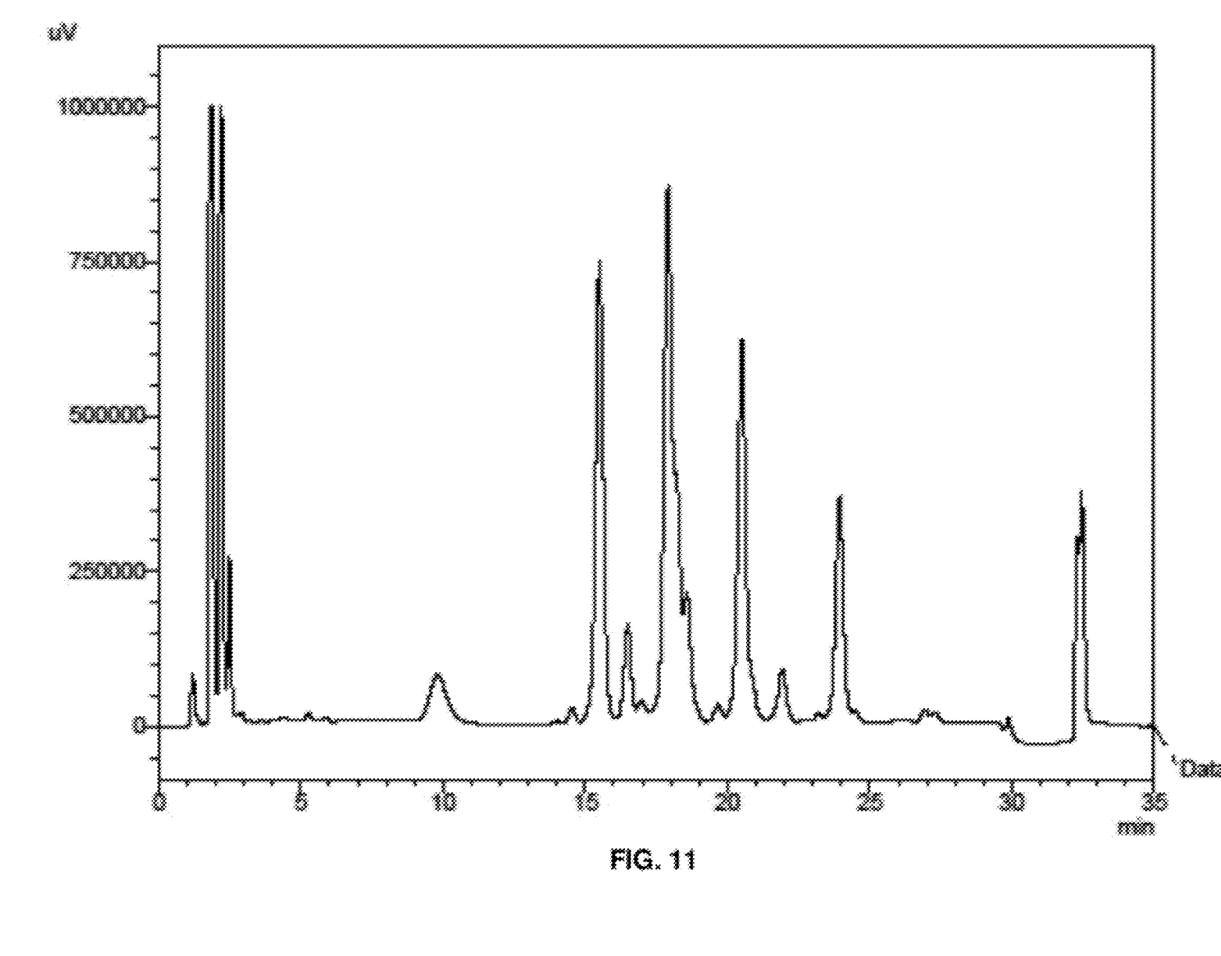
FIG. 11 shows an HPLC profile of N-glycans released from immobilized IgG by solubilized PNGase F enzyme using the spin column system of the present invention.

Samples containing 25 µg hIgG were loaded on protein A spin columns and washed as described in Example 2. Following the wash, the spin columns and racks were moved to an empty, unused receiver plate. A 10 µL volume of PNGase F enzyme (Glyconase, ProZyme, Inc., Hayward, Calif.) was pipetted into the sample cups, and the assemblies were centrifuged at 200×g for 2 minutes to expose the protein A-bound IgG to the enzyme. The assemblies were then placed on an incubator block as described herein and incubated at 70° C. for 15 minutes. The enzyme released N-linked glycans from the IgG into solution. Following the incubation, the released glycans were eluted from the spin columns by pipetting in 20 µL of elution buffer and centrifuging the assemblies at 200×g for 2 minutes. The receiver plates were removed from the spin columns and racks. The released N-glycans were then fluorescently labeled and analyzed by normal phase HPLC with fluorescent detection using standard methods (reagents and columns provided by ProZyme). The resulting N-glycan HPLC profile is shown in FIG. 11, and is very similar to published profiles for hIgG N-glycans produced by conventional solution phase methods.

We claim:

1. A spin column system comprising:
   at least one spin column having a packed bed;
   a rack having
      a top panel comprising a lower surface; and
      a side panel comprising a bottom surface;
      at least one aperture passing through the top panel, wherein the aperture is dimensioned and configured to releasably engage the at least one spin column therein; and
   a receiver plate or a microplate comprising:
      a top panel comprising an upper surface;
      at least one well defined within the top panel corresponding to the at least one aperture in the rack, the at least one well having a bottom surface; and
      a well opening in a plane defined by the top panel,
   wherein the rack is configured to engage the receiver plate or the microplate;
   wherein the rack and the receiver plate are dimensioned and configured to engage one another, wherein the lower surface of the top panel of the rack contacts the upper surface of the top panel of the receiver plate such that the aperture and the at least one well are in register when the rack and the receiver plate are engaged, and further wherein the packed bed is disposed entirely between the bottom surface and the well opening when the rack and the receiver plate are engaged and the at least one spin column is disposed in the aperture, and
   wherein the rack and the microplate are configured to engage one another, wherein the bottom surface of the side panel of the rack contacts the upper surface of the top panel of the microplate such that the aperture and the at least one well are in register when the rack and the microplate are engaged, and further wherein an outlet tip of the spin column is within 5 mm of the well opening when the rack and the microplate are engaged and the at least one spin column is disposed in the aperture.

2. The system of claim 1, wherein the rack is dimensioned and configured to engage with the microplate wherein the rack and the spin column are dimensioned and configured to suspend the outlet tip within 5 mm of the well opening of the microplate.

3. The system of claim 1, wherein the rack is dimensioned and configured to engage with the microplate and a volume capacity of the packed bed is at least about 5-fold lower than a volume capacity of the well of the microplate.

4. The system of claim 3, wherein the volume capacity of the packed bed is at least about 10-fold lower than the volume capacity of the well of the microplate.

5. The system of claim 1, wherein the packed bed having a volume capacity of about 60 µL or less.

6. The system of claim 1, wherein the rack is dimensioned and configured to engage with the microplate, wherein the side panel comprising a lip offset from the side panel, the lip comprising an inner surface, and wherein the bottom surface and the inner surface both contact the microplate, when the rack and the microplate are engaged.

7. The system of claim 1, wherein the rack is dimensioned and configured to engage with a conventional 96-well microplate.

8. The system of claim 1, wherein the rack, the spin column, and the receiver plate are dimensioned and configured to suspend the outlet tip within 5 mm of the bottom surface of the well.

9. The system of claim 1, wherein the rack further comprises a lip offset from the side panel and the receiver plate further comprises a side panel and a lip offset from the side panel, and wherein the side panel and the lip of the rack contacts the side panel and the lip of the receiver plate, respectively, when the rack and the receiver plate are engaged.

10. The system of claim 9, wherein the side panel of the rack also contacts the lip of the receiver plate when the rack and the receiver plate are engaged.

11. The system of claim 1, wherein the at least one aperture of the rack comprises 96 apertures and the at least one well of the receiver plate comprises 96 wells, and the 96 apertures and the 96 wells are arranged in an 8×12 array on 9 mm centers.

12. The system of claim 1, further comprising a lid dimensioned and configured to engage with the rack and contact the spin column.

13. The system of claim 12, wherein the spin column further comprises a sample cup in fluid communication with the packed bed and having an upper rim, and wherein the sample cup, the packed bed, and the well together form a substantially sealed chamber when the rack and the spin column, the rack and the receiver plate, and the lid and the rack are engaged and further when the rack contacts the upper rim of the spin column.

14. The system of claim 13, wherein the spin column and the rack form a continuous contact when the spin column is inserted in the rack, the rack and the receiver plate form a continuous contact when the rack and the receiver plate are engaged; and the lid and the upper rim of the spin column form a continuous contact when the lid is engaged with the rack and the lid contacts the spin column.

15. The system of claim 1, further comprising an incubator block dimensioned and configured to contact an outer surface of the well of the receiver plate and to heat and cool to a specified temperature.

16. The system of claim 1, further comprising a lid and an incubator block, wherein the lid, the spin column, the receiver plate, and the incubator block are configured and dimensioned to assemble in a nested configuration.

17. A method of analyzing an analyte with the system of claim 1 comprising: (a) inserting the spin column in the aperture in the rack and engaging the rack with the receiver plate, wherein the spin column, the rack, and the receiver plate form an assembled unit, and wherein the spin column is in register with the well in the receiver plate; (b) loading a sample in the spin column; (c) spinning the assembled unit, wherein an analyte in the sample binds to a packed bed in the spin column; (d) eluting the analyte or a derivative thereof from the packed bed; and (e) analyzing the analyte or derivative thereof.

18. The method of claim 17 wherein the spinning includes spinning the assembled unit in a centrifuge under a centrifugal force such that the analyte is quantitatively bound and retained in the packed bed.

19. The method of claim 17 wherein the eluting includes adding to the spin column a volume of an elution buffer at least five times a volume capacity of the packed bed, spinning the assembled unit, and collecting eluate in the well, wherein the well has a volume capacity at least 5-fold greater than the volume capacity of the packed bed.

20. The method of claim 19 wherein the well has a volume capacity at least 10-fold greater than the volume capacity of the packed bed, and wherein the analyzing includes adding to the well a volume of an analytical reagent at least equal to the volume of the elution buffer, mixing the eluate and the analytical reagent to create a mixture, and reading the mixture.

21. The method of claim 17 wherein the analyzing includes quantitating an amount of the analyte or the derivative thereof.

22. The method of claim 17 further comprising, after the analyzing step, removing the spin column from the rack and repeating steps (a)-(e) with a second spin column using the rack.

23. The method of claim 17 further comprising rewetting the packed bed, wherein the rewetting comprises adding an amount of liquid to the spin column and spinning the assembled unit, wherein the amount of liquid fills the well to a level at least equal to an interface between the packed bed and a sample cup in the spin column, wherein a portion of liquid remains in the sample cup after spinning, and wherein air is removed from the packed bed.

24. The method of claim 17 further including, between the spinning step and the eluting step, removing the rack from the receiver plate and engaging the rack with a conventional 96-well microplate such that apertures in the rack are in registration with wells of the microplate when the rack is engaged with the microplate, wherein the eluting includes collecting eluate in a well of the microplate.

25. The method of claim 17 further including engaging a lid with the rack to form a substantially sealed chamber comprising a sample cup of the spin column, the packed bed, and the well of the receiver plate, wherein evaporation is minimized.

26. The method of claim 25 further including incubating the packed bed of the receiver plate in an incubator block, wherein an amount of heat is transferred from the incubator block through a well wall in the well and through liquid contained in the well to the packed bed, wherein temperature of the packed bed and the incubator block are the same and evaporation is minimized.

27. The method of claim 17 further including, after the eluting step, incubating wells of the receiver plate in an incubator block to promote evaporation.

28. The method of claim 17 further including, between the spinning and the eluting steps, exchanging a solution comprising a catalytic reagent into the packed bed, wherein the catalytic agent chemically modifies the analyte bound to the packed bed to generate a derivative of the analyte.

29. The method of claim 28 further including, between the exchanging and the eluting steps, incubating the packed bed of the receiver plate in an incubator block, wherein an amount of heat is transferred from the incubator block through a well wall in the well and through liquid contained in the well to the packed bed, wherein temperature of the packed bed and the incubator block are the same and evaporation is minimized.

30. The method of claim 29 further including prior to the incubating step, engaging a lid with the rack to form a substantially sealed chamber comprising a sample cup of the spin column, the packed bed, and the well of the receiver plate, wherein evaporation is minimized.

31. The method of claim 28 wherein the derivative of the analyte is released from the packed bed prior to the eluting step.

* * * * *

UNITED STATES PATENT AND TRADEMARK OFFICE
CERTIFICATE OF CORRECTION

PATENT NO. : 8,377,394 B2
APPLICATION NO. : 12/835886
DATED : February 19, 2013
INVENTOR(S) : Robert Sakowski et al.

Page 1 of 1

It is certified that error appears in the above-identified patent and that said Letters Patent is hereby corrected as shown below:

On Title page, field (73), in "Assignee", in column 1, line 1, delete "Technoogies," and insert -- Technologies, --, therefor.

In column 22, line 23, in claim 2, after "microplate" insert -- , --.

Signed and Sealed this
Ninth Day of April, 2013

Teresa Stanek Rea
*Acting Director of the United States Patent and Trademark Office*